US006066476A

United States Patent [19]
Tsien et al.

[11] Patent Number: 6,066,476
[45] Date of Patent: *May 23, 2000

[54] MODIFIED GREEN FLUORESCENT PROTEINS

[75] Inventors: Roger Y. Tsien, La Jolla; Roger Heim, Del Mar, both of Calif.

[73] Assignee: The Regents of the University of California, Oakland, Calif.

[*] Notice: This patent is subject to a terminal disclaimer.

[21] Appl. No.: 08/753,144

[22] Filed: Nov. 20, 1996

Related U.S. Application Data

[60] Division of application No. 08/727,452, filed as application No. PCT/US95/14692, Nov. 13, 1995, which is a continuation-in-part of application No. 08/337,915, Nov. 10, 1994, Pat. No. 5,625,048.

[51] Int. Cl.$^7$ .......................... C12P 21/04; C12N 15/00; C07K 1/00
[52] U.S. Cl. ..................... 435/69.7; 435/440; 530/350; 530/855
[58] Field of Search .................... 435/69.7, 440; 530/350, 855

[56] References Cited

U.S. PATENT DOCUMENTS

| | | | |
|---|---|---|---|
| 5,264,563 | 11/1993 | Huse | 536/25.3 |
| 5,491,084 | 2/1996 | Chalfie | 435/189 |
| 5,625,048 | 4/1997 | Tsien et al. | 536/23.4 |
| 5,741,668 | 4/1998 | Ward et al. | 435/69.1 |
| 5,777,079 | 7/1998 | Tsien et al. | 530/350 |

FOREIGN PATENT DOCUMENTS

| | | |
|---|---|---|
| 0 428 000 A1 | 5/1991 | European Pat. Off. . |
| WO 91/01305 | 2/1991 | WIPO . |
| WO 94/28166 | 8/1994 | WIPO . |
| WO 95/21191 | 8/1995 | WIPO . |
| WO 95/07463 | 3/1996 | WIPO . |
| 96/23898 | 8/1996 | WIPO . |
| WO 96/23810 | 8/1996 | WIPO . |
| 96/27027 | 9/1996 | WIPO . |
| 96/27675 | 9/1996 | WIPO . |
| WO 97/11094 | 3/1997 | WIPO . |
| WO 97/28261 | 8/1997 | WIPO . |

OTHER PUBLICATIONS

Heim et al., "Engineering green fluorescent protein for improved brightness, longer wavelengths and fluorescence resonance energy tranfer," *Current Biology* 6(2): 178–182 (1996).
Inouye and Tsuji, "Expression of the gene and fluorescence characteristics of the recombinant protein," *FEBS Letters* 341: 277–280 (1994).
Mitra et al., "Fluorescence resonance energy transfer between blue–emitting and red–shifted excitation derivatives of the green fluorescent protein," *Gene* 173(1): 13–17 (Jul. 1, 1996).
Roth, Thesis from the Graduate Program in Biochemistry from Rutgers, the State University of New Jersey (Oct. 1985).
Baldwin et al., Biochemistry 29:5509–9915 (1990).
Chalfie et al., Science 263:802–805 (1994).
Cody et al., Biochemistry 32:1212–1218 (1993).
Cubitt et al., Trends in Biochem. Sci. 20:488–455 (1995).
Delagrave et al., Bio/Technology 13:151–154 (1995).
Deschamps et al., Protein Expression and Purification, 6:555–558 (1995).
Ehrig et al., FEBS Letters 367:163–166 (1995).
Heim et al., Proc. Natl. Acad. Sci. U.S.A. 91:12501–12505 (1994).
Heim et al. Nature 373:663–664 (1995).
Kain et al, Bio Techniques 19:650–655 (1995).
Levine et al., Comp. Biochem. Physiol. 728:77–85 (1982).
Muhlrad et al., Yeast 8:79–82 (1992).
Norris et al., Plant Molecular Biology, 24:673–677 (1994).
Prasher et al., Gene 111:229–233 (1992).
Sala–Newby et al, Biochem. J. 279:727–732 (1991).
Surpin et al., Photochem. Photobiol. 49:Abstract, 25S (1989).
Ward, in Bioluminescence and Chemiluminescence (eds. DeLuca et al., 235–242 (Academic Press, New York, 1981).
Ward et al., Biochemistry 21:4535–4540 (1982).
Ward et al., Photochem. Photobiol. 35:803–808 (1982).
Wilbanks et al., J. Biol. Chem. 268:1226–1235 (1993).

*Primary Examiner*—Robert A. Wax
*Assistant Examiner*—Elizabeth Slobodyansky
*Attorney, Agent, or Firm*—Fish & Richardson P.C.

[57] ABSTRACT

Modifications in the sequence of Aequorea wild-type GFP provide products having markedly different excitation and emission spectra from corresponding products from wild-type GFP. In one class of modifications, the product derived from the modified GFP exhibits an alteration in the ratio of two main excitation peaks observed with the product derived from wild-type GFP. In another class, the product derived from the modified GFP fluoresces at a shorter wavelength than the corresponding product from wild-type GFP. In yet another class of modifications, the product derived from the modified GFP exhibits only a single excitation peak and enhanced emission relative to the product derived from wild-type GFP.

5 Claims, 7 Drawing Sheets

MODIFIED GREEN FLUORESCENT PROTEINS

This application is a divisional application of U.S. application Ser. No. 08/727,452, filed Oct. 18 1996 which is a 371 of PCT application Ser. No. PCT/US95/14692, filed Nov. 13, 1995, which is a continuation-in-part of U.S. application Ser. No. 08/337,915 filed Nov. 10, 1994, which issued as U.S. Pat. No. 5,625,048 on Apr. 29, 1997.

BACKGROUND OF THE INVENTION

This invention relates generally to the fields of biology and chemistry. More particularly, the invention is directed to modified fluorescent proteins and to methods for the preparation and use thereof.

This invention was made with Government support under Grant No. NS27177, awarded by the National Institute of Health. The Government has certain rights in this invention.

In biochemistry, molecular biology and medical diagnostics, it is often desirable to add a fluorescent label to a protein so that the protein can be easily tracked and quantified. The normal procedures for labeling requires that the protein be covalently reacted in vitro with fluorescent dyes, then repurified to remove excess dye and any damaged protein. If the labeled protein is to be used inside cells, it usually has to be microinjected; this is a difficult and time-consuming operation that cannot be performed on large numbers of cells. These problems may, however, be eliminated by joining a nucleotide sequence coding for the protein of interest with the sequence for a naturally fluorescent protein, then expressing the fusion protein.

The green fluorescent protein (GFP) of the jellyfish *Aequorea Victoria* is a remarkable protein with strong visible absorbance and fluorescence from a p-hydroxybenzylideneimidazolone chromophore, which is generated by cyclization and oxidation of the protein's own Ser-Tyr-Gly sequence at positions 65 to 67. A cDNA sequence [SEQ ID NO:1] for one isotype of GFP has been reported [Prasher, D. C. et al., *Gene* 111, 229–233 (1992)]; cloning of this cDNA has enabled GFP expression in different organisms. The finding that the expressed protein becomes fluorescent in cells from a wide variety of organisms [Chalfie, M. et al., *Science* 263, 802–805 (1994)] makes GFP a powerful new tool in molecular and cell biology and indicates that the oxidative cyclization must be either spontaneous or dependent only on ubiquitous enzymes and reactants.

A major question in protein photophysics is how a single chromophore can give widely different spectra depending on its local protein environment. This question has received the most attention with respect to the multiple colors of visual pigments based on retinal [Merbs, S. L. & Nathans, J. *Science* 258, 464–466 (1992)], but is also important in GFP. The GFP from Aequorea and that of the sea pansy *Renilla reniformis* share the same chromophore, yet Aequorea GFP has two absorbance peaks at 395 and 475 nm, whereas Renilla GFP has only a single absorbance peak at 498 nm, with about 5.5 fold greater monomer extinction coefficient than the major 395 nm peak of the Aequorea protein [Ward, W. W. in *Bioluminescence and Chemiluminescence* (eds. DeLuca, M.A. & McElroy, W.D.) 235–242 (Academic Press, New York, 1981)]. The spectra of the isolated chromophore and denatured protein at neutral pH do not match the spectra of either native protein [Cody, C. W. et al., *Biochemistry* 32, 1212–1218 (1993)].

For many practical applications, the spectrum of Renilla GFP would be preferable to that of Aequorea, because wavelength discrimination between different fluorophores and detection of resonance energy transfer are easier if the component spectra are tall and narrow rather than low and broad. Furthermore, the longer wavelength excitation peak (475 nm) of Aequorea GFP is almost ideal for fluorescein filter sets and is resistant to photobleaching, but has lower amplitude than the shorter wavelength peak at 395 nm, which is more susceptible to photobleaching [Chalfie et al. (1994), supra]. For all these reasons, it would clearly be advantageous to convert the Aequorea GFP excitation spectrum to a single peak, and preferably at longer wavelengths.

There is also a need in the art for proteins which fluoresce at different wavelengths. Variants of fluorescent proteins with different colors would also be very useful for simultaneous comparisons of multiple protein fates, developmental lineages, and gene expression levels.

Accordingly, it is an object of the present invention to provide improved fluorescent proteins which do not suffer from the drawbacks of native Aequorea GFP.

SUMMARY OF THE INVENTION

In accordance with the present invention, it has been determined that particular modifications in the polypeptide sequence of an Aequorea wild-type GFP [SEQ ID NO:2] lead to formation of products having markedly different excitation and emission spectra from corresponding products derived from wild-type GFP. Visibly distinct colors and/or increased intensities of emission make these products useful in a wide variety of contexts, such as tracking of differential gene expression and protein localization.

BRIEF DESCRIPTION OF THE DRAWINGS

The invention may be better understood with reference to the accompanying drawings, in which.

DETAILED DESCRIPTION OF THE INVENTION

GFP was expressed in *E. coli* under the control of a T7 promoter for quantitative analysis of the properties of the recombinant protein. Gel electrophoresis under denaturing conditions showed protein of the expected molecular weight (27 kDa) as a dominant band (FIG. 1), which could be quantified simply by densitometry of staining with Coomassie blue. Soluble recombinant GFP proved to have identical spectra and the same or even slightly more fluorescence per mole of protein as GFP purified from *Aequorea victoria*, showing that the soluble protein in *E. coli* undergoes correct folding and oxidative cyclization with as high an efficiency as in the jellyfish.

Figure 1:
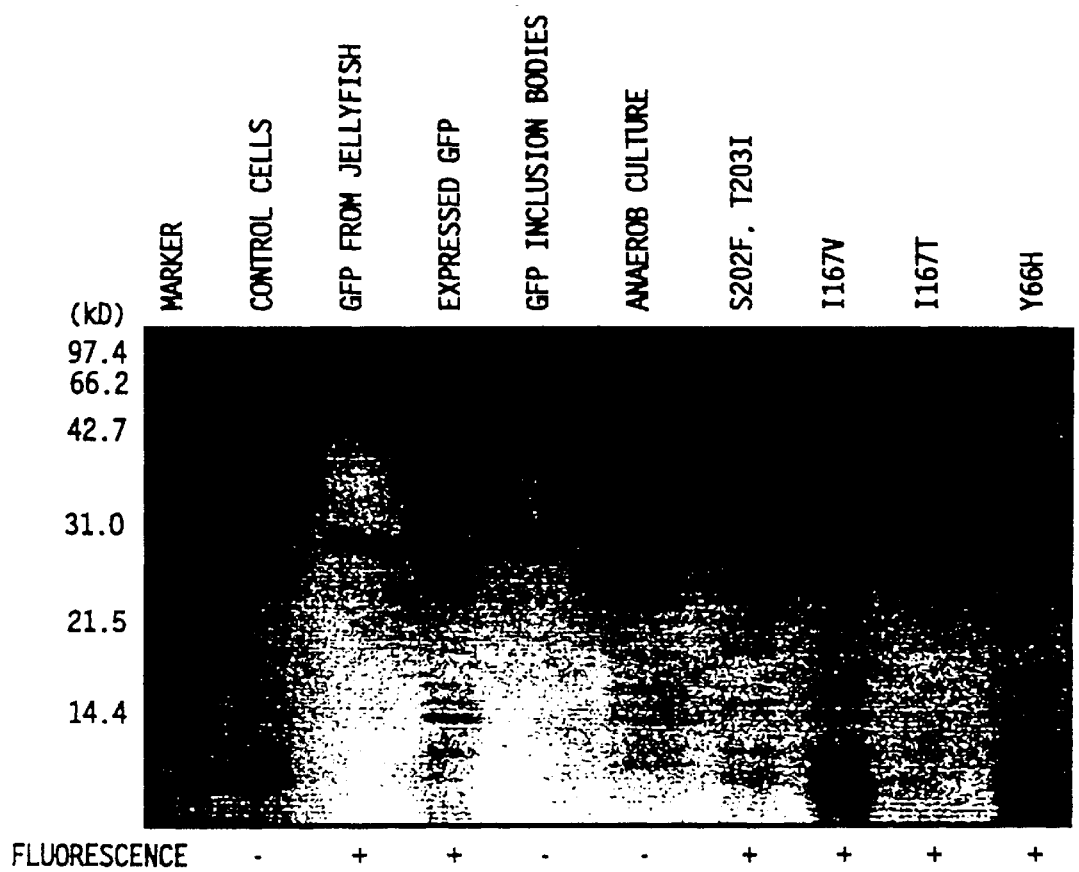
FIG. 1 compares different versions of GFP by gel electrophoresis and Coomassie blue staining.

The bacteria also contained inclusion bodies consisting of protein indistinguishable from jellyfish or soluble recombinant protein on denaturing gels (FIG. 1). However, this material was completely non-fluorescent, lacked the visible absorbance bands of the chromophore, and could not be made fluorescent even when solubilized and subjected to protocols that renature GFP [Ward, W. W. & Bokman, S. H., *Biochemistry* 21, 4535–4540 (1982); Surpin, M. A. & Ward, W. W., *Photochem. Photobiol.* 49, Abstract, 25S (1989)]. Therefore, protein from inclusion bodies seemed permanently unable to generate the internal chromophore. An interesting intermediate stage in protein maturation could be generated by growing the bacteria anaerobically. The soluble protein again looked the same as GFP on denaturing gels (FIG. 1) but was non-fluorescent. In this case, fluorescence gradually developed after admission of air, even when fresh protein synthesis was blocked using puromycin and tetracycline. Evidently, the soluble non-fluorescent protein synthesized under anaerobic conditions was ready to become fluorescent once atmospheric oxygen was readmitted. The fluorescence per protein molecule approached its final asymptotic value with a single-exponential time course and a rate constant of $0.24\pm0.06$ $hr^{-1}$ (at 22° C.) measured either in intact cells with protein-synthesis inhibitors or in a lysate in which the soluble proteins and cofactors were a thousand fold more dilute. Such pseudo-first order kinetics strongly suggest that no enzymes or cofactors are necessary for the final step of fluorophore formation in GFP.

It has thus been determined that formation of the final fluorophore requires molecular oxygen and proceeds in wild-type protein with a time constant of ~4 h at 22° C. and atmospheric $pO^2$. This was independent of dilution, implying that the oxidation does not require enzymes or cofactors.

Figure 2:
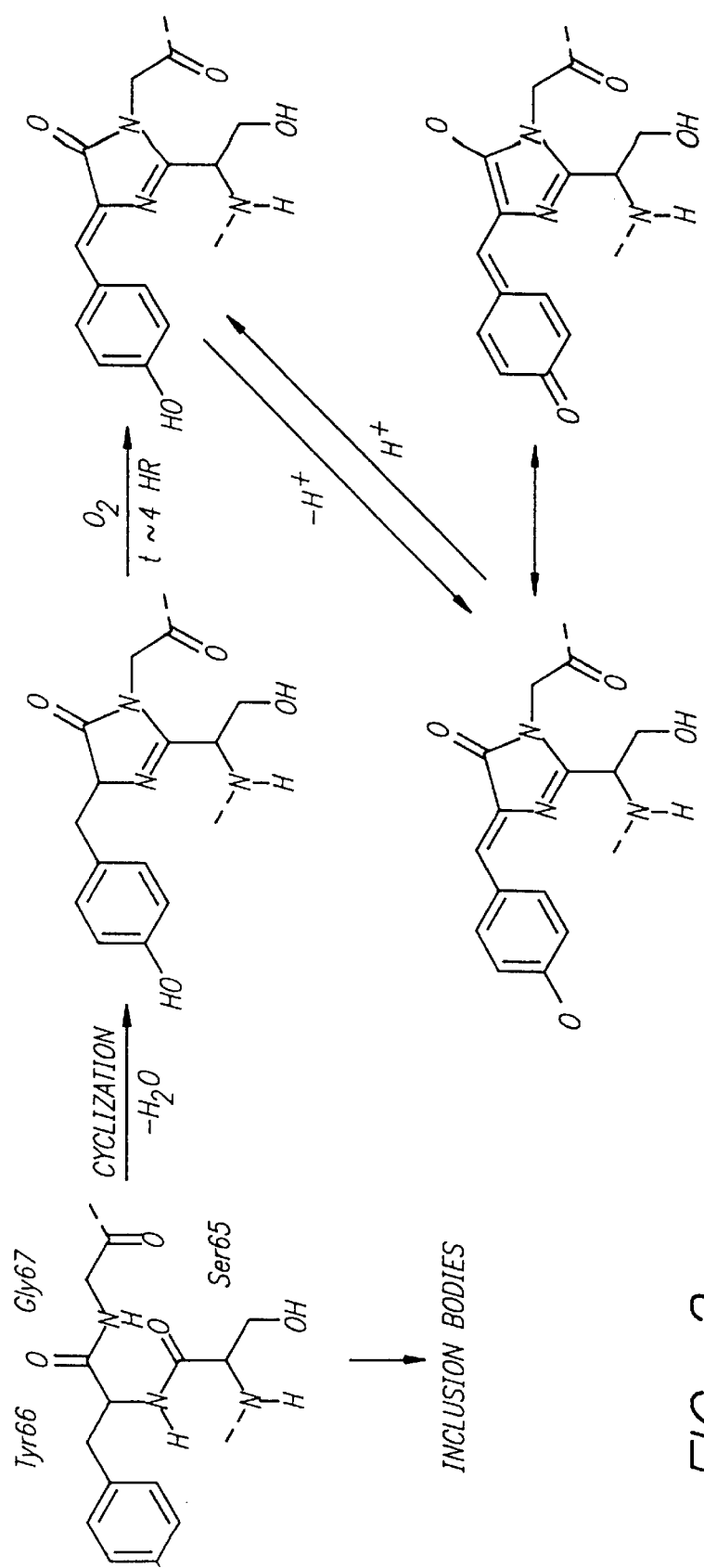
FIG. 2 illustrates a proposed biosynthetic scheme for GFP.

A molecular interpretation is presented in FIG. 2. If the newly translated apoprotein (top left) evades precipitation into inclusion bodies, the amino group of Gly 67 might cyclize onto the carbonyl group of Ser 65 to form an imidazolidin-5-one, where the process would stop (top center) if $O_2$ is absent. The new N=C double bond would be expected to promote dehydrogenation to form a conjugated chromophore; imidazolidin-5-ones are indeed known to undergo autoxidative formation of double bonds at the 4-position [Kjaer, A. *Acta Chem. Scand.* 7, 1030–1035 (1953); Kidwai, A. R. & Devasia, G. M. *J. Org. Chem.* 27, 4527–4531 (1962)], which is exactly what is necessary to complete the fluorophore (upper right). The protonated and deprotonated species (upper and lower right) may be responsible for the 395 and 470–475 nm excitation peaks, respectively. The excited states of phenols are much more acidic than their ground states, so that emission would come only from a deprotonated species.

The Aequorea GFP cDNA was subjected to random mutagenesis by hydroxylamine treatment or polymerase chain reaction. Approximately six thousand bacterial colonies on agar plates were illuminated with alternating 395 and 475 nm excitation and visually screened for altered excitation properties or emission colors.

According to a first aspect of the present invention, modifications are provided which result in a shift in the ratio of the two excitations peaks of the product after oxidation and cyclization relative to the wild type. Three mutants were found with significant alterations in the ratio of the two main excitation peaks (Table I). The mutations were sequenced and recombined with the wild-type gene in different ways to eliminate neutral mutations and assign the fluorescence effects to single amino acid substitutions, except for H9 where two neighboring mutations have not yet been separated. They all lay in the C terminal part of the protein (Table I), remote in primary sequence from the chromophore formed from residues 65–67.

These and other modifications are defined herein with reference to the amino acid sequence [SEQ ID NO:2] encoded by the reported cDNA [SEQ ID NO:1]; the first amino acid identified is the one found at the indicated location in the reported sequence, while the second indicates the substitution found in the modified form. The fluorescent product derived from a wild-type or modified GFP polypeptide sequence is no longer strictly speaking a simple polypeptide after oxidation and cyclization; however, reference is sometimes made for sake of simplicity herein to the polypeptide (e.g., "wild-type GFP" or "modified GFP") where what is intended would be obvious from the context. Compared with wild-type GFP, H9 (Ser 202→Phe, Thr 203→Ile) had increased fluorescence at 395 nm excitation; P9 (Ile 167→Val) and P11 (Ile 167→Thr) were more fluorescent at 475 nm excitation.

One possibility for these spectral perturbations in P9 and P11 is that the mutations at Ile 167 shift a positive charge slightly closer to the phenolic group of the fluorophore; this should both increase the percentage of phenolic anion, which is probably the species responsible for the 470–475 nm excitation peak, and shift the emission peak hypsochromically. However, the hypothesized ionizable phenolic group would have to be buried inside the protein at normal pH, because the ratio of 471 to 396 nm peaks in the mutants could not be further affected by external pH until it was raised to 10, just below the threshold for denaturation. The pH-sensitivity of wild-type GFP is similar [Ward, W. W. et al., *Photochem. Photobiol.* 35, 803–808 (1982)].

According to another aspect of the invention, a mutant P4 (Tyr 66→His) was identified which was excitable by ultraviolet and fluoresced bright blue in contrast to the green of wild type protein. The excitation and emission maxima were hypsochromically shifted by 14 and 60 nm respectively from those of wild-type GFP. The mutated DNA was sequenced and found to contain five amino acid substitutions, only one of which proved to be critical: replacement of Tyr 66 in the center of the chromophore by His (corresponding to a change in the GFP cDNA sequence [SEQ ID NO:1] at 196–198 from TAT to CAT).

The surprising tolerance for substitution at this key residue prompted further site-directed mutagenesis to Trp and Phe at this position. Trp gave excitation and emission wavelengths intermediate between Tyr and His (Table I) but was only weakly fluorescent, perhaps due to inefficiency of folding or chromophore formation due to steric considerations. Phe gave weak fluorescence with an excitation maximum at 358 nm and an emission maximum at 442 nm. Accordingly, pursuant to this aspect of the invention modified GFP proteins which fluoresce at different wavelengths (preferably, different by at least 10 nm and more preferably, by at least 50 nm) relative to the native protein are provided, for example, those wherein Tyr 66 is replaced by Phe, His or Trp.

In a further embodiment of this aspect of the invention, a double mutant Y66H, Y145F was identified which had almost the same wavelengths as the single mutant Y66H but almost twice the brightness, due mainly to a higher quantum efficiency of fluorescence. The double mutant also developed its fluorescence during overnight growth, whereas the single mutant required several days.

In accordance with further embodiments of this aspect of the invention, a first round of mutagenesis to increase the brightness of Y66W yielded M153T/V163A/N212K as additional substitutions. This mutant was subjected to another round of mutagenesis, resulting in two further sets, N146I and I123V/Y145H/H148R (Table II). The quantum efficiency of these mutants is now comparable to wild-type GFP. The clustering of the substitutions in residues 145 to 163 suggest that those residues lie relatively close to the chromophore and that reductions in the size of their side chains might be compensating for the larger size of tryptophan compared to tyrosine.

Pursuant to yet another aspect of the present invention, modified GFP proteins are provided which provide substantially more intense fluorescence per molecule than the wild type protein. Modifications at Ser 65 to Ala, Leu, Cys, Val, Ile or Thr provide proteins with red-shifted and brighter spectra relative to the native protein. In particular, the Thr mutant (corresponding to a change in the GFP cDNA sequence [SEQ ID NO:1] at 193–195 from TCT to ACT) and Cys mutant (corresponding to a change in the GFP cDNA sequence [SEQ ID NO:1] at 193–195 from TCT to TGT) are about six times brighter than wild type when excited at the preferred long-wavelength band above 450 nm. As a consequence, these modified proteins are superior to wild type proteins for practically all applications. Further, the brightness of these modified proteins matches the brightness reported in the literature for Renilla GFP; thus, these proteins clearly obviate the objections to the dimness of Aequorea GFP. In fact, it is speculated that the chromophores in these modified proteins may exhibit the optimum brightness which could be achieved with a general structure derived from the Aequorea GFP chromophore. In particular, these mutations provide products exhibiting one or more of the following salient characteristics which distinguish them clearly over the corresponding product from a wild-type GFP: reduced efficiency of excitation by wavelengths between about 350 and 420 nm; enhanced excitation and emission efficiency when excited with wavelengths longer than about 450 nm; increased resistance to light-induced shifts in the excitation spectrum; and faster kinetics of fluorophore generation. In contrast, mutations to Trp, Arg, Asn, Phe and Asp did not provide improved brightness.

Mutagenesis of S65T to shift its wavelengths further to the red yielded M153A/K238E (Table II) as the GFP variant with the longest-wavelength excitation maximum yet described, 504 nm vs. 490 nm for S65T. Surprisingly, the emission peak hardly changed (514 nm vs. 511 nm), so that the separation between the excitation and emission peaks (Stokes' shift) is extremely narrow, only 10 nm. This is one of the smallest values reported for any fluorophore in aqueous solution at room temperature. As in the Y66W series, M153 seems to be influential. It is doubtful that K238E is important, because this substitution has been found to be without effect in other mutants.

As would be readily apparent to those working in the field, to provide the desired fluorescent protein it would not be necessary to include the entire sequence of GFP. In particular, minor deletions at either end of the protein sequence are expected to have little or no impact on the fluorescence spectrum of the protein. Therefore, by a mutant or wild-type GFP sequence for purposes of the present invention are contemplated not only the complete polypeptide and oligonucleotide sequences discussed herein, but also functionally-equivalent portions thereof (i.e., portions of the polypeptide sequences which exhibit the desired fluorescence properties and oligonucleotide sequences encoding these polypeptide sequences). For example, whereas the chromophore itself (position 65–67) is obviously crucial, the locations of known neutral mutations suggest that amino acids 76–115 are less critical to the spectroscopic properties of the product. In addition, as would be immediately apparent to those working in the field, the use of various types of fusion sequences which lengthen the resultant protein and serve some functional purpose in the preparation or purification of the protein would also be routine and are contemplated as within the scope of the present invention. For example, it is common practice to add amino acid sequences including a polyhistidine tag to facilitate purification of the product proteins. As such fusions do not significantly alter the salient properties of the molecules comprising same, modified GFPs as described herein including such fusion sequences at either end thereof are also clearly contemplated as within the scope of the present invention.

Similarly, in addition to the specific mutations disclosed herein, it is well understood by those working in the field that in many instances modifications in particular locations in the polypeptide sequence may have no effect upon the properties of the resultant polypeptide. Unlike the specific mutations described in detail herein, other mutations provide polypeptides which have properties essentially or substantially indistinguishable from those of the specific polypeptides disclosed herein. For example, the following substitutions have been found to be neutral (i.e., have no significant impact on the properties of the product): Lys 3→Arg; Asp 76→Gly; Phe 99→Ile; Asn 105→Ser; Glu 115→Val; Thr 225→Ser; and Lys 238→Glu. These equivalent polypeptides (and oligonucleotide sequences encoding these polypeptides) are also regarded as within the scope of the present invention. In general, the polypeptides and oligonucleotide sequences of the present invention (in addition to containing at least one of the specific mutations identified herein) will be at least about 85% homologous, more preferably at least about 90% homologous, and most preferably at least about 95% homologous, to the wild-type GFP described herein. Because of the significant difference in properties observed upon introduction of the specified modifications into a GFP sequence, the presence of the specified modifications relative to the corresponding reported sequence for wild-type GFP [SEQ ID NO:2] are regarded as central to the invention.

The oligonucleotide sequences of the present invention are particularly useful in processes for labelling polypeptides of interest, e.g., by the construction of genes encoding fluorescent fusion proteins. Fluorescence labeling via gene fusion is site-specific and eliminates the present need to purify and label proteins in vitro and microinject them into cells. Sequences encoding the modified GFPs of the present invention may be used for a wide variety of purposes as are well known to those working in the field. For example, the sequences may be employed as reporter genes for monitoring the expression of the sequence fused thereto; unlike other reporter genes, the sequences require neither substrates nor cell disruption to evaluate whether expression has be achieved. Similarly, the sequences of the present invention may be used as a means to trace lineage of a gene fused thereto during the development of a cell or organism. Further, the sequences of the present invention may be used as a genetic marker; cells or organisms labeled in this manner can be selected by, e.g., fluorescence-activated cell sorting. The sequences of the present invention may also be used as a fluorescent tag to monitor protein expression in vivo, or to encode donors or acceptors for fluorescence resonance energy transfer. Other uses for the sequences of the present invention would be readily apparent to those working in the field, as would appropriate techniques for fusing a gene of interest to an oligonucleotide sequence of the present invention in the proper reading frame and in a suitable expression vector so as to achieve expression of the combined sequence.

The availability of several forms of GFP with such different spectral properties should facilitate two-color assessment of differential gene expression, developmental fate, or protein trafficking. For example, if one wanted to screen for a drug that is specific to activate expression of gene A but not gene B, one could fuse the cDNA for one color of GFP to the promoter region of gene A and fuse the cDNA for another color to the promoter region of gene B. Both constructs would be transfected into target cells and the candidate drugs could be assayed to determine if they stimulate fluorescence of the desired color, but not fluorescence of the undesired color. Similarly, one could test for the simultaneous expression of both A and B by searching for the presence of both colors simultaneously.

As another example, to examine the precise temporal or spatial relationship between the generation or location of recombinant proteins X and Y within a cell or an organism, one could fuse genes for different colors of GFP to the genes for proteins X and Y, respectively. If desired, DNA sequences encoding flexible oligopeptide spacers could be included to allow the linked domains to function autonomously in a single construct. By examining the appearance of the two distinguishable colors of fluorescence in the very same cells or organisms, one could compare and contrast the generation or location of the proteins X and Y with much greater precision and less biological variability than if one had to compare two separate sets of cells or organisms, each containing just one color of GFP fused to either protein X or Y. Other examples of the usefulness of two colors would be obvious to those skilled in the art.

The further mutations to brighten the Y66H and Y66W variants of GFP enhance the possibility of using two or three colors of fluorescent protein to track differential gene expression, protein localizations or cell fates. For example, mutants P4–3 (Y66H/Y145F), W7 (Y66W/N146I/M153T/V163A/N212K) and S65T can all be distinguished from each other. P4–3 is specifically detected by exciting at 290–370 nm and collecting emission at 420–460 nm. W7 is specifically detected by exciting at 410–457 nm and collecting emission at 465–495 nm. S65T is specifically detected by exciting at 483–493 nm and collecting emission at wavelengths greater than 510 nm. Bacteria carrying these three proteins are readily discriminated under a microscope using the above wavelength bandpass filters.

The chromophore in GFP is well buried inside the rest of the protein, so much of the dimness of the original point mutants was presumably due to steric mismatch between the substituted amino acid and the cavity optimized for tyrosine. The location of the beneficial mutations implies that residues 145–163 are probably close to the chromophore. The M153A/S65T mutant has the longest wavelengths and smallest Stokes' shift of any known fluorescent protein that does not use a cofactor.

The invention may be better understood with reference to the accompanying examples, which are intended for purposes of illustration only and should not be construed as in any sense limiting the scope of the invention as defined by the claims appended hereto.

EXAMPLE 1

The coding region of GFP clone 10.1 [Prasher et al. (1992), supra] was amplified by PCR to create NdeI and BamHI sites at the 5' and 3' ends, respectively, and was cloned behind the T7 promoter of pGEMEX2 (Promega) replacing most of the T7 gene 10. The resulting plasmid was transformed into the strain JM109(DE3) (Promega Corp., Madison, Wis.), and high level expression was achieved by growing the cultures at 24° C. to saturation without induction by IPTG. To prepare soluble extracts, 1.5 ml cell suspension were collected, washed and resuspended in 150 µl 50 mM Tris/HCl, pH 8.0, 2 mM EDTA. Lysozyme and DNAse I were added to 0.2 mg/ml and 20 µg/ml, respectively, and the samples were incubated on ice until lysis occurred (1–2 hours). The lysates were then clarified by centrifuging at 12,000×g for 15 minutes. Inclusion bodies were obtained as described in the literature [Sambrook, J. et al. in *Molecular Cloning: A Laboratory Manual* Vol. 2, 17.37–17.41 (Cold Spring Harbor Press, Cold Spring Harbor, N.Y., 1989)].

As illustrated in FIG. 1, soluble extracts of *E. coli* expressing GFP show a predominant band which is absent in extracts from control cells and has the same electrophoretic mobility as native GFP isolated from the jellyfish *A. Victoria*. Inclusion bodies of expressing cells consist mainly of non-fluorescent GFP which has the same mobility as soluble GFP. Non-fluorescent soluble GFP of anaerobically grown cultures is also a major band with correct mobility. Soluble extracts of the mutated clones H9, P9, P11 and P4 again contain a dominant protein with essentially the same molecular weight.

Random mutagenesis of the GFP cDNA was done by increasing the error rate of the polymerase chain reaction with 0.1 mM $MnCl_2$, 50 µM dATP and 200 µM of dGTP, dCTP, and dTTP [Muhlrad, D. et al., *Yeast* 8, 79–82 (1992)]. The product was ligated into pGEMEX2 and subsequently transformed into JM109(DE3). Colonies on agar were visually screened for different emission colors and ratios of brightness when excited at 475 vs. 395 um.

Figure 3A:
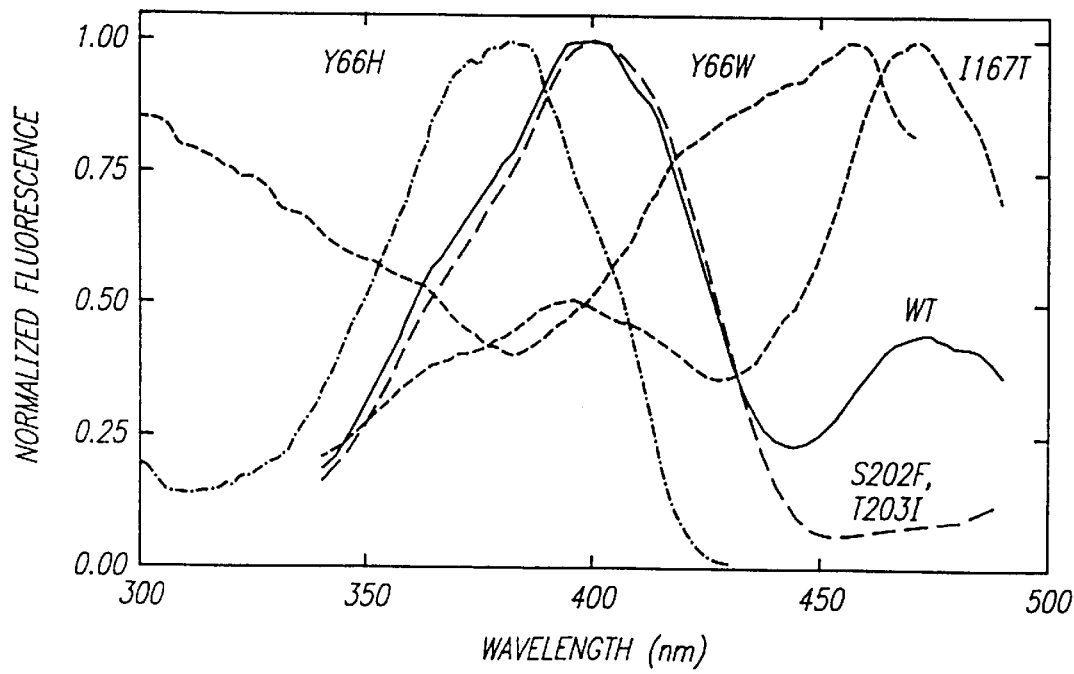
FIGS. 3a and 3b illustrate the excitation and emission spectra of wild-type and a first group of mutant GFPs.
Figure 3B:
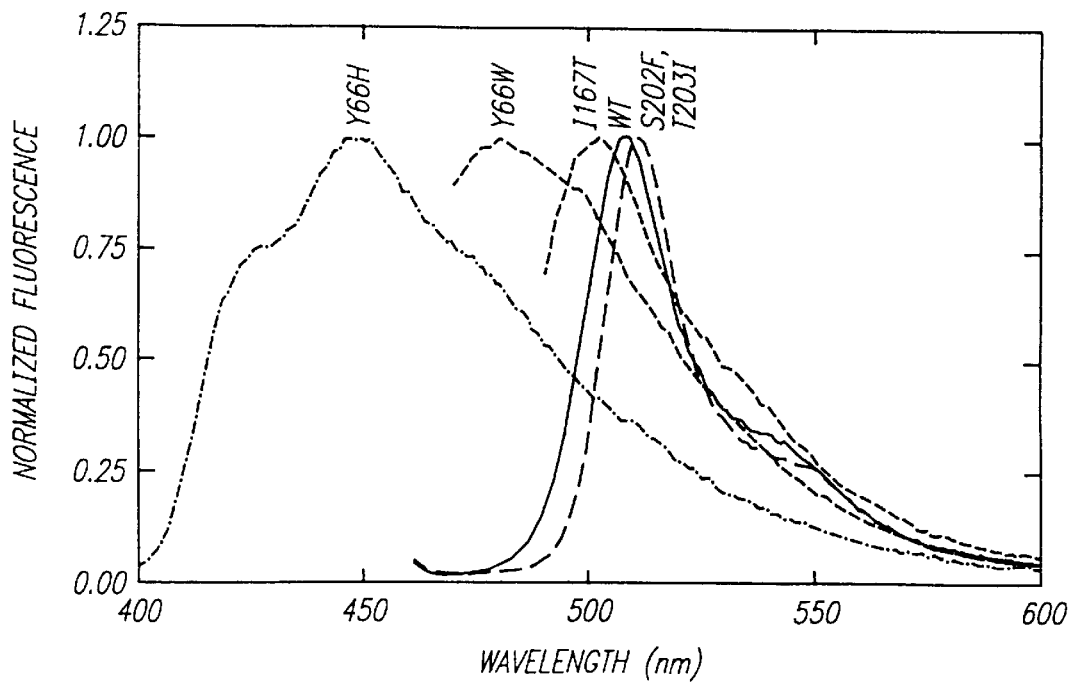

FIGS. 3a and 3b illustrate the excitation and emission spectra of wild-type and mutant GFPs. In FIGS. 3a and 3b, ——— wild-type; ——— S202F, T203I; - - - I167T; - - - Y66W; —•—• Y66H. Samples were soluble fractions from *E. coli* expressing the proteins at high level, except for Y66W, which was obtained in very low yield and measured on intact cells. Autofluorescence was negligible for all spectra except those of Y66W, whose excitation spectrum below 380 nm may be contaminated by autofluorescence. Excitation and emission spectra were measured with 1.8 nm bandwidths and the non-scanning wavelength set to the appropriate peak. Excitation spectra were corrected with a rhodamine B quantum counter, while emission spectra (except for Y66W) were corrected for monochromator and detector efficiencies using manufacturer-supplied correction spectra. All amplitudes have been arbitrarily normalized to a maximum value of 1.0. A comparison of brightness at equal protein concentrations is provided in Table I.

TABLE I

Characteristics of mutated vs. wild-type GFP

| Variant | Mutation | Excitation Maxima (nm)[a] | Emission Maxima (nm)[b] | Relative[c] Fluorescence |
|---|---|---|---|---|
| Wild type | none | 396 (476) | 508 (503) | (≡100%) |
| H9 | Ser 202→Phe, Thr 203→Ile | 398 | 511 | 117%[d] |
| P9 | Ile 167→Val | 471 (396) | 502 (507) | 166%[e] |

TABLE I-continued

Characteristics of mutated vs. wild-type GFP

| Variant | Mutation | Excitation Maxima (nm)[a] | Emission Maxima (nm)[b] | Relative[c] Fluorescence |
|---|---|---|---|---|
| P11 | Ile 167→Thr | 471 (396) | 502 (507) | 188%[c] |
| P4 | Tyr 66→His | 382 | 448 | 57%[f] |
| W | Tyr 66→Trp | 458 | 480 | n.d. |

[a]Values in parentheses are lower-amplitude peaks.
[b]Primary values were observed when exciting at the main excitation peak; values in parentheses were observed when illuminating at the lower-amplitude excitation peak.
[c]Equal amounts of protein were used based on densitometry of gels stained with Coomassie Blue (FIG. 1).
[d]Emission maxima of spectra recorded at excitation 395 nm were compared.
[e]Emission maxima of spectra recorded at excitation 475 nm were compared.
[f]Emission spectrum of P4 recorded at 378 nm excitation was integrated and compared to the integrated emission spectrum of wild type recorded at 475 nm excitation; both excitation and emission characteristics were corrected.

EXAMPLE 2

Oligonucleotide-directed mutagenesis at the codon for Ser-65 of GFP cDNA was performed by the literature method [Kunkel, T.A. (1985) *Proc. Natl. Acad. Sci. USA* 82, 488] using the Muta-Gene Phagemid in Vitro Mutagenesis Kit version 2, commercially available from Bio-Rad, Richmond, Calif. The method employs a bacterial host strain deficient for dUTPase (dut) and uracil-N-glycosylase (ung), which results in an occasional substitution of uracil for thymine in newly-synthesized DNA. When the uracil-containing DNA is used as a wild-type template for oligonucleotide-directed in vitro mutagenesis, the complementary (mutant) strand can be synthesized in the presence of deoxynucleotides, ligase and polymerase using the mutagenic oligonucleotide to prime DNA synthesis; the Version 2 kit utilizes unmodified T7 DNA polymerase to synthesize the complementary strand. When the heteroduplex molecule is transformed into a host with an active uracil-N-glycosylase (which cleaves the bond between the uracil base and the ribose molecule, yielding an apyrimidic site), the uracil-containing wild-type strand is inactivated, resulting in an enrichment of the mutant strand.

The coding region of GFP cDNA was cloned into the BamHI site of the phagemid pRSETB from Invitrogen (San Diego, Calif.). This construct was introduced into the dut, ung double mutant *E. coli* strain CJ236 provided with the Muta-Gene kit and superinfected with helper phage VCSM13 (Stratagene, La Jolla, Calif.) to produce phagemid particles with single-stranded DNA containing some uracils in place of thymine. The uracil-containing DNA was purified to serve as templates for in vitro synthesis of the second strands using the mutagenic nucleotides as primers. The DNA hybrids were transformed into the strain XL1blue (available from Stratagene), which has a functional uracil-N-glycosylase; this enzyme inactivates the parent wild-type DNA strand and selects for mutant clones. DNA of several colonies were isolated and checked for proper mutation by sequencing.

To express the mutant proteins, the DNA constructs obtained by mutagenesis were transformed into *E. coli* strain BL21(DE3)LysS (Novagen, Madison, Wis.), which has a chromosomal copy of T7 polymerase to drive expression from the strong T7 promotor. At room temperature 3 ml cultures were grown to saturation (typically, overnight) without induction. Cells from 1 ml of culture were collected, washed and finally resuspended in 100 μl of 50 mM Tris pH 8.0, 300 mnM NaCl. The cells were then lysed by three cycles of freeze/thawing (liquid nitrogen/30° C. water bath). The soluble fraction was obtained by pelletting cell debris and unbroken cells in a microfuge.

To facilitate purification of the recombinant proteins, the vector used fuses a histidine tag (6 consecutive His) to the N-terminus of the expressed proteins. The strong interaction between histidine hexamers and $Ni^{2+}$ ions permitted purification of the proteins by NI-NTA resin (available commercially from Qiagen, Chatsworth, Calif.). Microcolumnns (10 μl bed volume) were loaded with 100 μl soluble extract (in 50 mM Tris pH 8.0, 300 mM NaCl), washed with 10 bed volumes of the same buffer and with 10 volumes of the buffer containing 20 mnM imidazole. The recombinant proteins were then eluted with the same buffer containing 100 mM imidazole.

Aliquots of the purified mutant GFP proteins were run along with wild-type GFP on a denaturing polyacrylamide gel. The gel was stained with Coomassie blue and the protein bands were quantified by scanning on a densitometer. Based on these results, equal amounts of each version of protein were used to run fluorescence emission and excitation spectra.

Figure 4A:
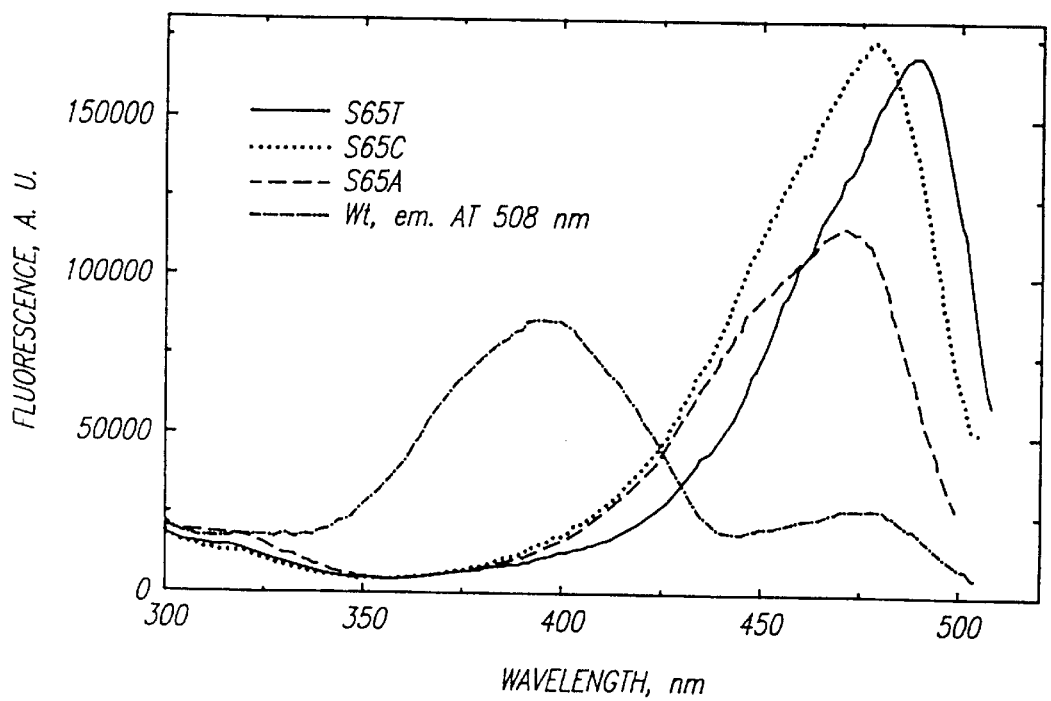
FIGS. 4a and 4b illustrate the excitation and emission spectra of wild-type and a second group of mutant GFPs.
Figure 4B:
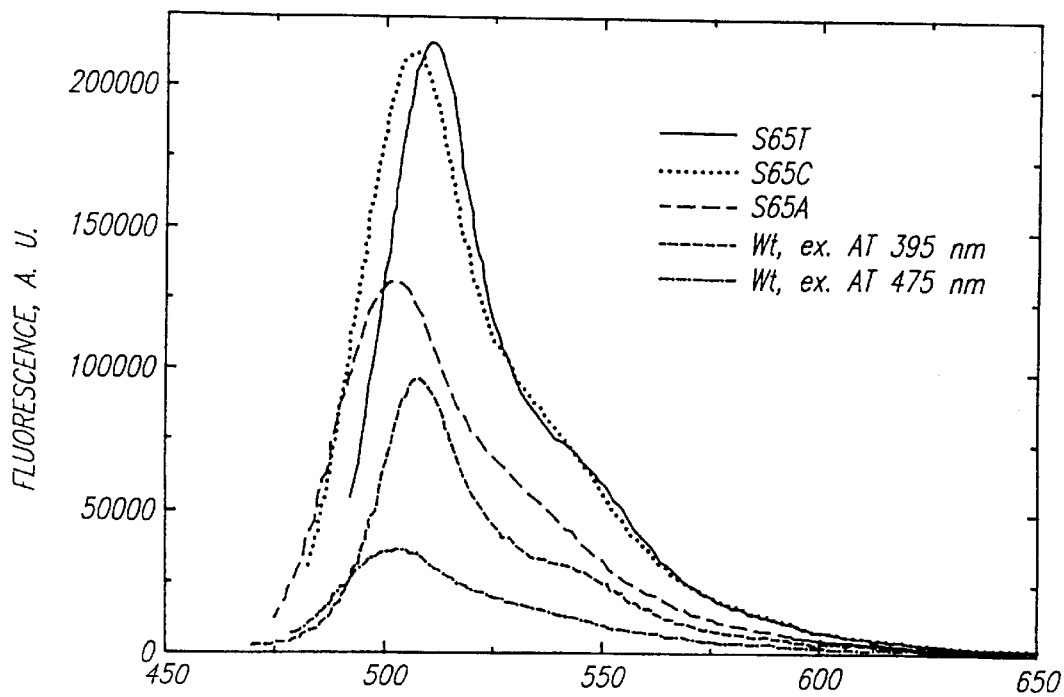

FIGS. 4a and 4b compare the excitation and emission spectra of wild-type and Ser 65 mutants. In FIG. 4a, —— S65T; —— S65A; - - - S 65C; —•—• wild-type (emission at 508 nm). In FIG. 4B, —— S65T; —— S65A; - - - S65C; ••• wild-type (excitation at 395 nm); —•—• wild-type (excitation at 475 nm). Excitation and emission spectra were measured with 1.8 rum bandwidths and the non-scanning wavelength set to the appropriate peak. As is apparent from FIG. 4b, all three mutants exhibited substantially higher intensity of emission relative to the wild-type protein.

Figure 5:
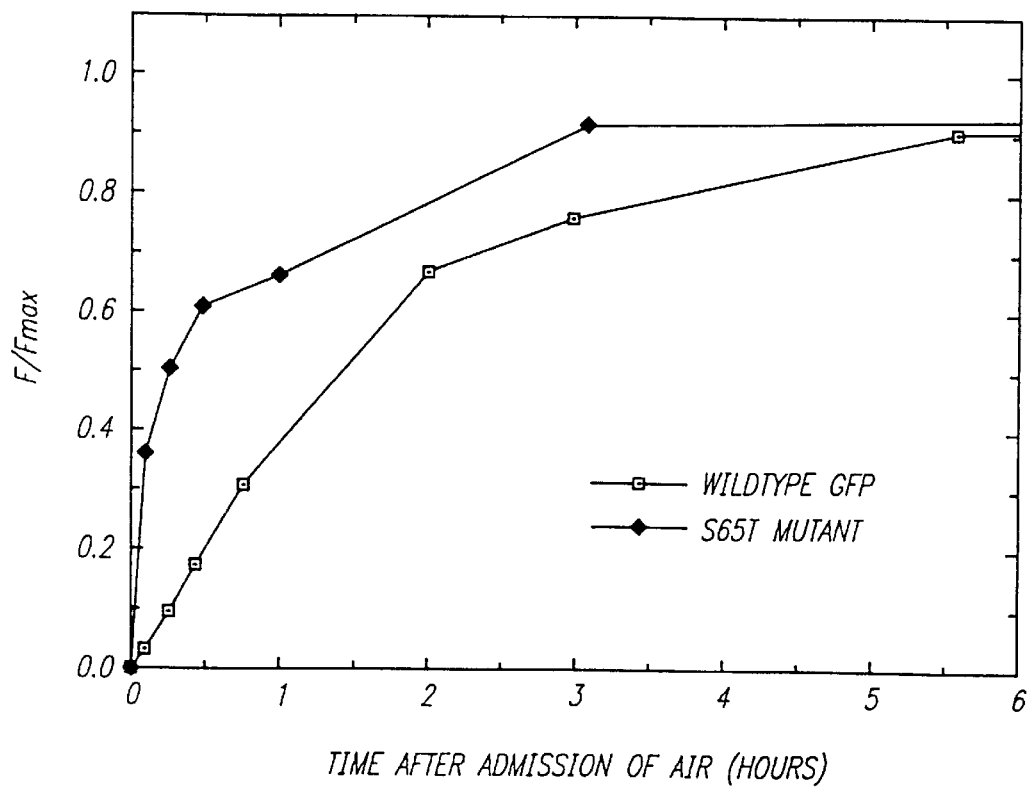
FIG. 5 illustrates the rate of fluorophore formation in the wild-type GFP and the Ser 65→Thr mutant.

FIG. 5 illustrates the rates of fluorophore formation in wild-type GFP and in the Ser 65→Thr mutant. *E. coli* expressing either wild-type or mutant GFP were grown anaerobically. At time=0, each sample was exposed to air; further growth and protein synthesis were prevented by transferring the cells to nutrient-free medium also containing sodium azide as a metabolic inhibitor. Fluorescence was subsequently monitored as a function of time. For each culture, the fluorescence intensities are expressed as a fraction of the final fluorescence intensity obtained at t=18 to 20 hours, after oxidation had proceeded to completion. From FIG. 5, it is apparent that development of fluorescence proceeds much more quickly in the mutant than in wild-type GFP, even after normalization of the absolute brightnesses (FIGS. 4a and 4b). Therefore, when the development of GFP fluorescence is used as an assay for promotor activation and gene expression, the mutant clearly gives a more rapid and faithful measure than wild-type protein.

Figure 6A:
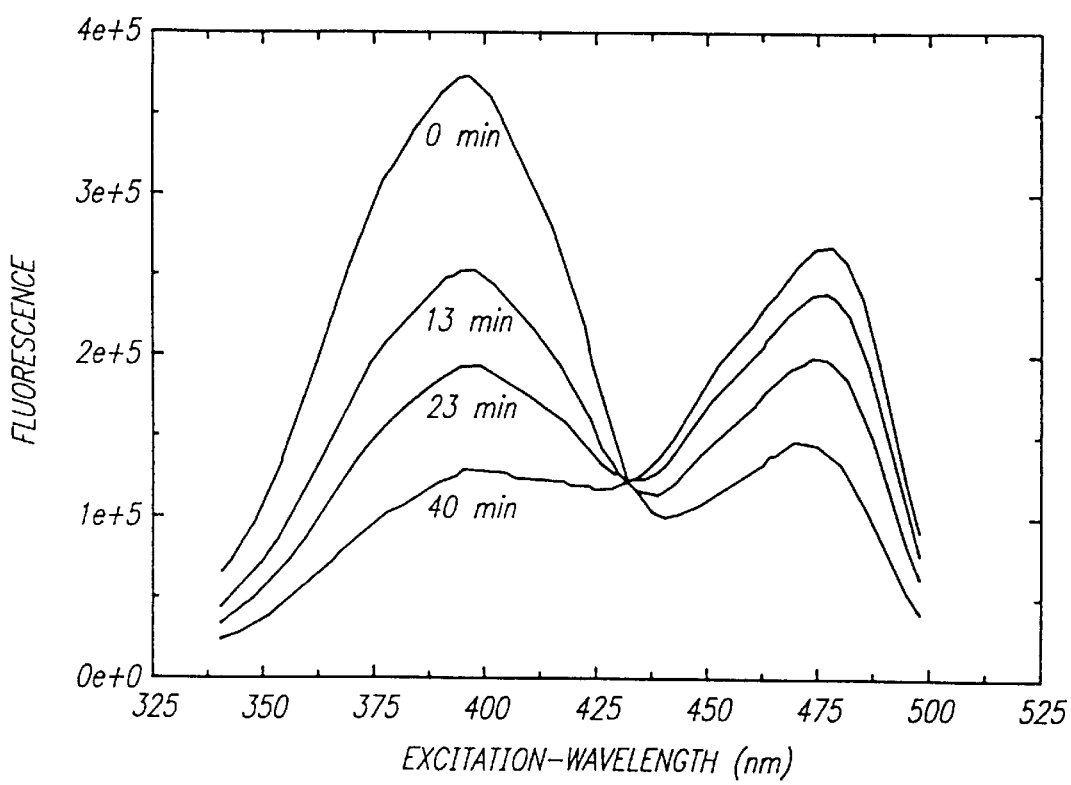
FIGS. 6a and 6b illustrate the behavior of wild-type GFP and the Ser 65→Thr mutant, respectively, upon progressive irradiation with ultraviolet light.
Figure 6B:
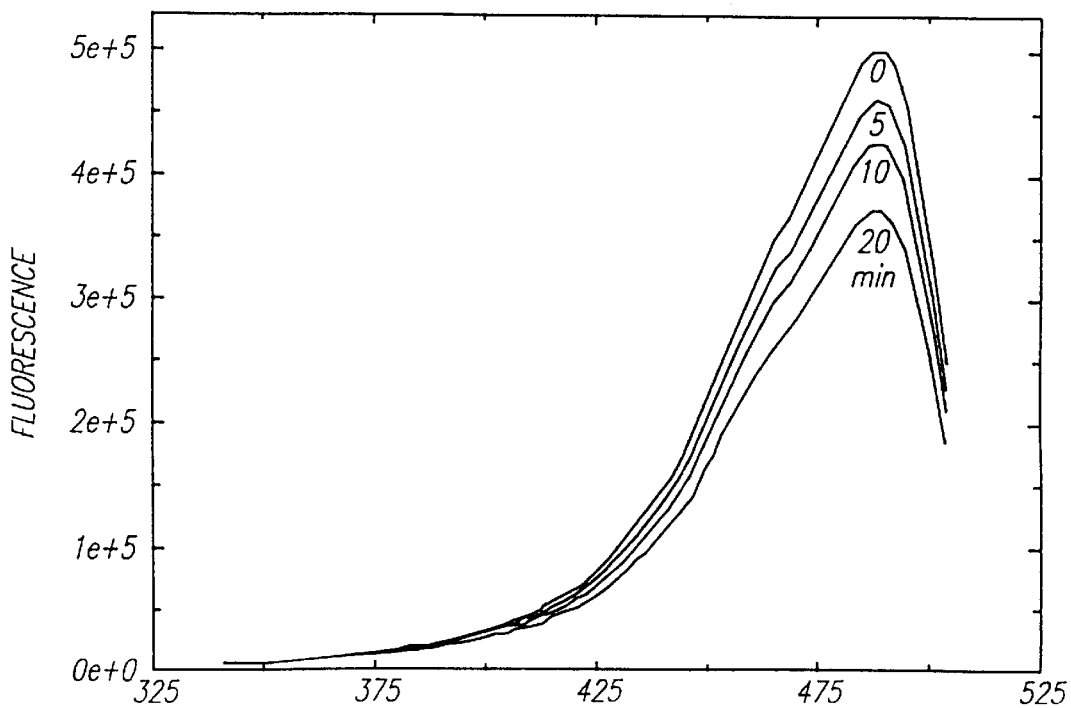

FIGS. 6a and 6b illustrate the behavior of wild-type GFP and the Ser 65→Thr mutant, respectively, upon progressive irradiation with ultraviolet light. Numbers indicate minutes of exposure to illumination at 280 nm; intensity was the same for both samples. Wild-type GFP (FIG. 6a) suffered photoisomerization, as shown by a major change in the shape of the excitation spectrum. Illumination with broad band (240–400 nm) UV caused qualitatively similar behavior but with less increase of amplitude in the 430–500 nm region of the spectrum. The photoisomerization was not reversible upon standing in the dark. This photoisomerization would clearly be undesirable for most uses of wild-type GFP, because the protein rapidly loses brightness when excited at its main peak near 395 nm. The mutant (FIG. 6b) showed no such photoisomerization or spectral shift.

EXAMPLE 3

GFP cDNAs encoding for Tyr66→His (Y66H), Tyr66→Trp (Y66W), or Ser65→Thr (S65T) were separately further mutagenized by the polymerase chain reaction and transformed into E. coli for visual screening of colonies with unusual intensities or colors. Isolation, spectral characterization (Table II and FIG. 7), and DNA sequencing yielded several additional useful variants.

Random mutagenesis of the gfp cDNA was done by increasing the error rate of the PCR with 0.1 mM $MnCl_2$ and unbalanced nucleotide concentrations. The GFP mutants S65T, Y66H and Y66W had been cloned into the BamHI site of the expression vector pRSETB (Invitrogen), which includes a T7 promoter and a polyhistidine tag. The GFP coding region (shown in bold) was flanked by the following 5' and 3' sequences: 5'-G GAT CCC CCC GCT GAA TTC ATG . . . AAA TAA TAA GGA TCC-3'. The 5' primer for the mutagenic PCR was the T7 primer matching the vector sequence; the 3' primer was 5'-GGT AAG CTT TTA TTT GTA TAG TTC ATC CAT GCC-3', specific for the 3' end of GFP, creating a HindIII restriction site next to the stop codon. Amplification was over 25 cycles (1 min at 94° C., 1 min 52° C., 1 min 72° C.) using the AmpliTaq polymerase from Perkin Elmer. Four separate reactions were run in which the concentration of a different nucleotide was lowered from 200 μM to 50 μM. The PCR products were combined, digested with BamHI and HindIII and ligated to the pRSETB cut with BamHI and HindIII. The ligation mixture was dialyzed against water, dried and subsequently transformed into the bacterial strain BL21(DE3) by electroporation (50 μl electrocompetent cells in 0.1 cm cuvettes, 1900 V, 200 ohm, 25 μF). Colonies on agar were visually screened for brightness as previously described herein. The selected clones were sequenced with the Sequenase version 2.0 kit from United States Biochemical.

Cultures with freshly transformed cells were grown at 37° C. to an optical density of 0.8 at 600 rn, then induced with 0.4 mM isopropylthiogalactoside overnight at room temperature. Cells were washed in PBS pH 7.4, resuspended in 50 mM Tris pH 8.0, 300 mM NaCl and lysed in a French press. The polyhistidine-tagged GFP proteins were purified from cleared lysates on nickel-chelate columns (Qiagen) using 100 mM imidazole in the above buffer to elute the protein.

Excitation spectra were obtained by collecting emission at the respective peak wavelengths and were corrected by a Rhodamine B quantum counter. Emission spectra were likewise measured at the respective excitation peaks and were corrected using factors from the fluorometer manufacturer (Spex Industries, Edison, NJ). In cleavage experiments emission spectra were recorded at excitation 368 nm. For measuring molar extinction coefficients, 20 to 30 μg of protein were used in 1 ml of PBS pH 7.4. Quantum yields of wild-type GFP, S65T, and P4–1 mutants were estimated by comparison with fluorescein in 0.1 N NaOH as a standard of quantum yield 0.91 [ed. Miller, J.N., *Standards in Fluorescence Spectrometry* (Chapman and Hall, New York, 1981)]. Mutants P4 and P4–3 were likewise compared to 9-amino-acridine in water (quantum yield 0.98). W2 and W7 were compared to both standards, which fortunately gave concordant results.

Figure 7:
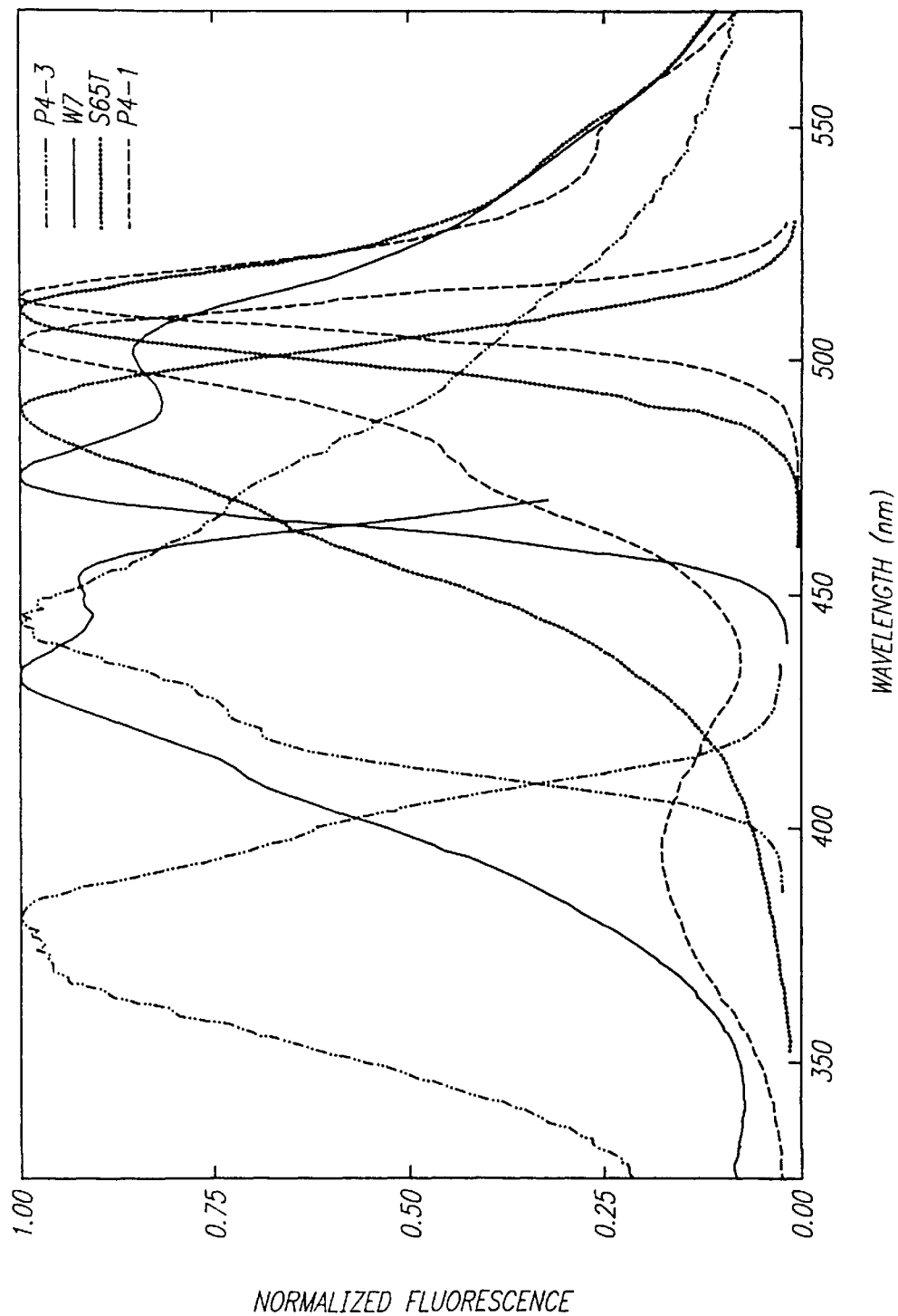
FIG. 7 illustrates fluorescence excitation and emission spectra of a third group of GFP mutants.

FIG. 7 illustrates the fluorescence excitation and emission spectra of different GFP mutants. All spectra were normalized to a maximal value of 1. Each pair of excitation and emission spectrum is depicted by a distinct line style.

The fluorescence properties of the obtained GFP mutants are reported in Table II.

TABLE II

| | | Fluorescence properties of GFP mutants | | | |
|---|---|---|---|---|---|
| Clone | Mutations | Excitation max (nm) | Emission max (nm) | Extinct.Coeff. ($M^{-1}cm^{-1}$) | Quantum yield |
| P4-3 | Y66H Y145F | 381 | 445 | 14,000 | 0.38 |
| W7 | Y66W N146I M153T V163A N212K | 433 (453) | 475 (501) | 18,000 (17,100) | 0.67 |
| W2 | Y66W I123V Y145H H148R M153T V163A N212K | 432 (453) | 480 | 10,000 (9,600) | 0.72 |
| P4-1 | S65T M153A K238E | 504 (396) | 514 | 14,500 (8,600) | 0.54 |

---

What is claimed is:

1. A functional mutant fluorescent protein, comprising:

a functional mutant fluorescent protein with an amino acid sequence that differs from an amino acid sequence of an Aequorea wild type green fluorescent protein (SEQ ID NO:2) by at least an aliphatic amino acid substitution at residue 65, wherein said functional mutant fluorescent protein has an excitation spectrum or emission spectrum different from an excitation spectrum or emission spectrum of said Aequorea wild type green fluorescent protein.

2. A fusion protein, comprising:

a functional mutant fluorescent protein with an amino acid sequence that differs from an amino acid sequence of an Aequorea wild type green fluorescent protein (SEQ ID NO:2) by at least one amino acid substitution at a residue selected from the group consisting of residue 65 and residue 66, wherein said substitution at residue 65 is an aliphatic substitution and a polypeptide of interest, wherein said functional mutant fluorescent protein has an excitation spectrum or emission spectrum different from an excitation spectrum or emission spectrum of said Aequorea wild type green fluorescent protein.

3. A fusion protein, comprising:

a functional mutant fluorescent protein with an amino acid sequence that differs from an amino acid sequence of an Aequorea wild type green fluorescent protein (SEQ ID NO:2) by at least one amino acid substitution at a residue selected from the group consisting of residue 65 and residue 66, and a polypeptide of interest, wherein said functional mutant fluorescent protein has an excitation spectrum or emission spectrum different from an excitation spectrum or emission spectrum of said Aequorea wild type green fluorescent protein, and wherein said fusion protein further comprises a flexible linker between said functional mutant fluorescent protein and said protein of interest.

4. A fusion protein, comprising:

a functional mutant fluorescent protein with an amino acid sequence that differs from an amino acid sequence of an Aequorea wild type green fluorescent protein (SEQ ID NO:2) by at least one amino acid substitution at a residue selected from the group consisting of residue 65 and residue 66, and a polypeptide of interest, wherein said functional mutant fluorescent protein has an excitation spectrum or emission spectrum different from an excitation spectrum or emission spectrum of said Aequorea wild type green fluorescent protein, and wherein said fusion protein further comprises a poly-histidine region.

5. The fusion protein of claim 4, wherein said poly-histidine region is at the amino-terminus of said fusion protein.

* * * * *

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
        (A) LENGTH: 716 base pairs
        (B) TYPE: nucleic acid
        (C) STRANDEDNESS: double -continued

```
        (D) TOPOLOGY: linear (ii) MOLECULE TYPE: cDNA (ix) FEATURE:
         (A) NAME/KEY: Coding Sequence
         (B) LOCATION: 1...715

(xi) SEQUENCE DESCRIPTION: SEQ ID NO:1:

ATG AGT AAA GGA GAA GAA CTT TTC ACT GGA GTT GTC CCA ATT CTT GTT         48
Met Ser Lys Gly Glu Glu Leu Phe Thr Gly Val Val Pro Ile Leu Val
 1               5                  10                  15

GAA TTA GAT GGT GAT GTT AAT GGG CAC AAA TTT TCT GTC AGT GGA GAG         96
Glu Leu Asp Gly Asp Val Asn Gly His Lys Phe Ser Val Ser Gly Glu
             20                  25                  30

GGT GAA GGT GAT GCA ACA TAC GGA AAA CTT ACC CTT AAA TTT ATT TGC        144
Gly Glu Gly Asp Ala Thr Tyr Gly Lys Leu Thr Leu Lys Phe Ile Cys
         35                  40                  45

ACT ACT GGA AAA CTA CCT GTT CCA TGG CCA ACA CTT GTC ACT ACT TTC        192
Thr Thr Gly Lys Leu Pro Val Pro Trp Pro Thr Leu Val Thr Thr Phe
     50                  55                  60

TCT TAT GGT GTT CAA TGC TTT TCA AGA TAC CCA GAT CAT ATG AAA CGG        240
Ser Tyr Gly Val Gln Cys Phe Ser Arg Tyr Pro Asp His Met Lys Arg
 65                  70                  75                  80

CAT GAC TTT TTC AAG AGT GCC ATG CCC GAA GGT TAT GTA CAG GAA AGA        288
His Asp Phe Phe Lys Ser Ala Met Pro Glu Gly Tyr Val Gln Glu Arg
                 85                  90                  95

ACT ATA TTT TTC AAA GAT GAC GGG AAC TAC AAG ACA CGT GCT GAA GTC        336
Thr Ile Phe Phe Lys Asp Asp Gly Asn Tyr Lys Thr Arg Ala Glu Val
            100                 105                 110

AAG TTT GAA GGT GAT ACC CTT GTT AAT AGA ATC GAG TTA AAA GGT ATT        384
Lys Phe Glu Gly Asp Thr Leu Val Asn Arg Ile Glu Leu Lys Gly Ile
        115                 120                 125

GAT TTT AAA GAA GAT GGA AAC ATT CTT GGA CAC AAA TTG GAA TAC AAC        432
Asp Phe Lys Glu Asp Gly Asn Ile Leu Gly His Lys Leu Glu Tyr Asn
    130                 135                 140

TAT AAC TCA CAC AAT GTA TAC ATC ATG GCA GAC AAA CAA AAG AAT GGA        480
Tyr Asn Ser His Asn Val Tyr Ile Met Ala Asp Lys Gln Lys Asn Gly
145                 150                 155                 160

ATC AAA GTT AAC TTC AAA ATT AGA CAC AAC ATT GAA GAT GGA AGC GTT        528
Ile Lys Val Asn Phe Lys Ile Arg His Asn Ile Glu Asp Gly Ser Val
                165                 170                 175

CAA CTA GCA GAC CAT TAT CAA CAA AAT ACT CCA ATT GGC GAT GGC CCT        576
Gln Leu Ala Asp His Tyr Gln Gln Asn Thr Pro Ile Gly Asp Gly Pro
            180                 185                 190

GTC CTT TTA CCA GAC AAC CAT TAC CTG TCC ACA CAA TCT GCC CTT TCG        624
Val Leu Leu Pro Asp Asn His Tyr Leu Ser Thr Gln Ser Ala Leu Ser
        195                 200                 205

AAA GAT CCC AAC GAA AAG AGA GAC CAC ATG GTC CTT CTT GAG TTT GTA        672
Lys Asp Pro Asn Glu Lys Arg Asp His Met Val Leu Leu Glu Phe Val
    210                 215                 220

ACA GCT GCT GGG ATT ACA CAT GGC ATG GAT GAA CTA TAC AAA TA            716
Thr Ala Ala Gly Ile Thr His Gly Met Asp Glu Leu Tyr Lys
225                 230                 235

(2) INFORMATION FOR SEQ ID NO:2:

(i) SEQUENCE CHARACTERISTICS:
        (A) LENGTH: 238 amino acids
        (B) TYPE: amino acid
        (D) TOPOLOGY: linear (ii) MOLECULE TYPE: protein
```

(v) FRAGMENT TYPE: internal (xi) SEQUENCE DESCRIPTION: SEQ ID NO:2:

Met Ser Lys Gly Glu Glu Leu Phe Thr Gly Val Val Pro Ile Leu Val
 1               5                  10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Ser Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235

(2) INFORMATION FOR SEQ ID NO:3:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

GGATCCCCCC GCTGAATTCA TG                                            22

(2) INFORMATION FOR SEQ ID NO:4:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

AAATAATAAG GATCC                                                    15

(2) INFORMATION FOR SEQ ID NO:5:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

GGTAAGCTTT TATTTGTATA GTTCATCCAT GCC    33